United States Patent
Wohrle et al.

(10) Patent No.: US 12,285,307 B2
(45) Date of Patent: Apr. 29, 2025

(54) SYSTEM AND METHOD FOR GUIDING MEDICAL INSTRUMENTS

(71) Applicants: Peter Wohrle, Corona Del Mar, CA (US); Oded Bahat, Beverly Hills, CA (US)

(72) Inventors: Peter Wohrle, Corona Del Mar, CA (US); Oded Bahat, Beverly Hills, CA (US)

( * ) Notice: Subject to any disclaimer, the term of this patent is extended or adjusted under 35 U.S.C. 154(b) by 0 days.

(21) Appl. No.: 15/047,545

(22) Filed: Feb. 18, 2016

(65) Prior Publication Data

US 2017/0231718 A1 Aug. 17, 2017

Related U.S. Application Data

(60) Provisional application No. 62/296,220, filed on Feb. 17, 2016.

(51) Int. Cl.
| | |
|---|---|
| *A61C 3/02* | (2006.01) |
| *A61C 1/00* | (2006.01) |
| *A61C 1/08* | (2006.01) |
| *A61C 19/04* | (2006.01) |
| *A61B 90/00* | (2016.01) |

(52) U.S. Cl.
CPC .............. *A61C 3/02* (2013.01); *A61C 1/0015* (2013.01); *A61C 1/082* (2013.01); *A61C 19/04* (2013.01); *A61B 2090/062* (2016.02)

(58) Field of Classification Search
CPC ........... A61C 3/02; A61C 1/082; A61C 19/04; A61B 17/1615; A61B 17/1622
USPC .............................. 433/165, 166, 32; 606/80
See application file for complete search history.

(56) References Cited

U.S. PATENT DOCUMENTS

| | | | | |
|---|---|---|---|---|
| 4,705,038 A | * | 11/1987 | Sjostrom | B23Q 5/00 D24/146 |
| 4,900,252 A | * | 2/1990 | Liefke | A61C 3/04 433/27 |
| 5,160,978 A | * | 11/1992 | Faville | G01B 11/10 702/158 |
| 5,178,536 A | * | 1/1993 | Werly | A61B 1/0623 348/66 |
| 5,269,794 A | * | 12/1993 | Rexroth | A61B 17/32002 606/167 |
| 5,400,267 A | * | 3/1995 | Denen | H02J 3/00 323/911 |
| 5,634,790 A | * | 6/1997 | Pathmanabhan | A61B 1/0607 433/29 |
| 5,902,105 A | * | 5/1999 | Uejima | H02J 7/00036 433/77 |
| 5,941,706 A | * | 8/1999 | Ura | A61B 17/16 433/165 |
| 5,947,729 A | * | 9/1999 | Bell | A61C 1/0015 433/98 |
| 6,213,771 B1 | * | 4/2001 | Fischer | A61C 5/42 433/102 |

(Continued)

*Primary Examiner* — Nicholas D Lucchesi
(74) *Attorney, Agent, or Firm* — Jason T. Daniel, Esq.; Daniel Law Offices, P.A.

(57) ABSTRACT

A system is disclosed. The system contains an instrument configured to fit in a patient's anatomy, an optical sensor associated with the instrument, a processing unit receiving data from the optical sensor, and a display displaying position of the instrument in the patient's anatomy based on the data from the optical sensor.

7 Claims, 9 Drawing Sheets

(56) References Cited

U.S. PATENT DOCUMENTS

| | | | | |
|---|---|---|---|---|
| 6,434,507 B1* | 8/2002 | Clayton | A61B 17/32002 | 600/104 |
| 6,468,076 B2* | 10/2002 | Kawamura | A61C 17/0202 | 433/29 |
| 6,752,626 B1* | 6/2004 | Rouiller | A61C 5/42 | 433/102 |
| 7,192,279 B2* | 3/2007 | Rogovsky | A61C 1/10 | 433/29 |
| 7,489,856 B2* | 2/2009 | Haller | B23Q 17/09 | 388/828 |
| 9,220,514 B2* | 12/2015 | Rains | A61B 17/7017 | |
| 9,480,538 B2* | 11/2016 | Yamashita | A61C 1/02 | |
| 10,306,124 B1* | 5/2019 | Rodriquez, Jr. | G03B 29/00 | |
| 2004/0209223 A1* | 10/2004 | Beier | A61C 19/002 | 433/126 |
| 2005/0282102 A1* | 12/2005 | Kert | A61B 5/0088 | 433/29 |
| 2006/0008771 A1* | 1/2006 | Courvoisier | A61B 17/16 | 433/165 |
| 2006/0085005 A1* | 4/2006 | Kenealy, III | A61B 17/1615 | 606/80 |
| 2006/0173291 A1* | 8/2006 | Glossop | A61B 90/96 | 600/424 |
| 2008/0224823 A1* | 9/2008 | Lawson | G06F 21/34 | 340/5.8 |
| 2008/0254404 A1* | 10/2008 | Heraud | A61C 1/0015 | 433/131 |
| 2008/0293008 A1* | 11/2008 | Regere | A61C 1/0015 | 433/119 |
| 2010/0109644 A1* | 5/2010 | Pruckner | G06K 19/07749 | 324/120 |
| 2011/0039229 A1* | 2/2011 | Senia | A61C 5/44 | 433/131 |
| 2011/0243673 A1* | 10/2011 | Svagr | B23B 31/16275 | 408/1 R |
| 2014/0005488 A1* | 1/2014 | Charles | A61B 17/02 | 606/80 |
| 2014/0107471 A1* | 4/2014 | Haider | A61B 17/1703 | 600/424 |
| 2014/0178832 A1* | 6/2014 | Choi | A61C 1/084 | 433/27 |
| 2014/0199650 A1* | 7/2014 | Moffson | A61B 5/682 | 600/409 |
| 2014/0272773 A1* | 9/2014 | Merritt | A61B 6/512 | 433/29 |
| 2015/0094836 A1* | 4/2015 | Rivers | B26D 5/007 | 700/160 |
| 2015/0374454 A1* | 12/2015 | Beerstecher | A61C 17/08 | 433/215 |
| 2018/0092708 A1* | 4/2018 | Cora | A61C 3/02 | |

\* cited by examiner

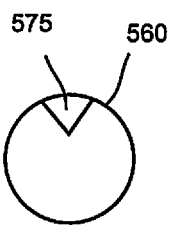 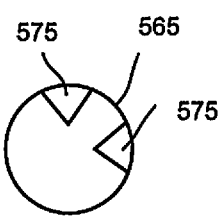 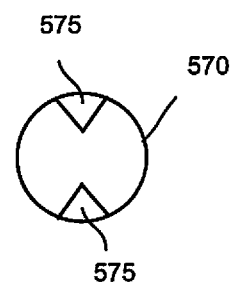
FIG. 4D   FIG. 4E   FIG. 4F

SYSTEM AND METHOD FOR GUIDING MEDICAL INSTRUMENTS

CROSS REFERENCE TO RELATED APPLICATIONS

This application claims the benefit of U.S. Provisional Application No. 62/296,220, filed on Feb. 17, 2016, which is incorporated herein by reference in its entirety.

FIELD

The present invention relates to field of medical devices. More particularly, the present invention relates to a system and method of guiding medical instruments.

BACKGROUND

Many different types of procedures are performed by dentists and dental surgeons using hand-held and hand-guided instruments to alter existing anatomy such as handpieces to operate rotary instruments (burrs, files, grinding wheels), and surgical tools that cut with emission of light (lasers) or electricity (cauterizing instruments) on teeth, facial bones, and soft tissues on patients. These procedures require skill and care to prevent damage to surrounding anatomical structures and host tissues. The procedures are often difficult to carry out because of the limited amount of space within the mouth of the patient's oral cavity that restricts the ability of the practitioner to align or move the tool during the course of the procedure. Frequently, the operating site is difficult to reach or to see, and nerves and blood vessels as well as cortical plates present additional challenges of not being easily identifiable during these procedures. Other factors such as patient movement can affect the precision and orientation of the tool with relation to the desired direction, and the precision of the surgical intervention.

The insertion of endosseous dental implants is an example of a procedure that illustrates the problem. Dental implant surgery involves placing an implant device, such as one or more artificial root replacements, in the jawbones of patients. Such devices must be precisely placed within the osseous supporting structures for the best implant survival, both in terms of success rates as well as quality of outcome. Precise placement of the endosseous device requires suitable preparation of the implant receptor site with respect to surrounding hard- and soft tissues. The entire final rehabilitation is typically comprised of a root replacement (the dental implant), an implant abutment, and a prosthetic replacement tooth, (or in combination of the two as a single piece), either as single tooth, multiple implants and teeth for a bridge in a partially edentulous patient, or a full arch bridge supported by multiple implants for full arch of teeth. During the surgical osteotomy preparation to create the bed for the implant to be inserted, great care must be taken to avoid causing injury to the patient. Injury may be caused by, for example, inadvertent entry into the mandibular nerve canal, inadvertent entry into the sinuses, perforation of the cortical plates, damage to adjacent teeth, or other damage known in the art.

In general there is a growing need to be able to provide systems that will reduce the risks associated with procedures carried out using dental instruments, as well as to improve outcome by idealizing implant location, and to maximize length, diameter and trajectory of the device. These new guiding systems must provide the surgeon with real time information that enables him/her to accurately guide his/her instrument(s).

Presently disclosed embodiments address the limitations known in the art.

BRIEF DESCRIPTION OF THE FIGURES

FIGS. 4c-f depict other embodiments according to the present disclosure.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Computed Tomography (CT) based dental 3D imaging is becoming an integral component to achieving success in dental procedures/surgeries. It can aid in treatment planning and clinically sound placement of, for example, implants and to avoid major critical structure such as inferior alveolar nerve or sinus. In planning a dental procedure/implant, a doctor creates a virtual plan based on the CT image data of a patient.

Figure 1:
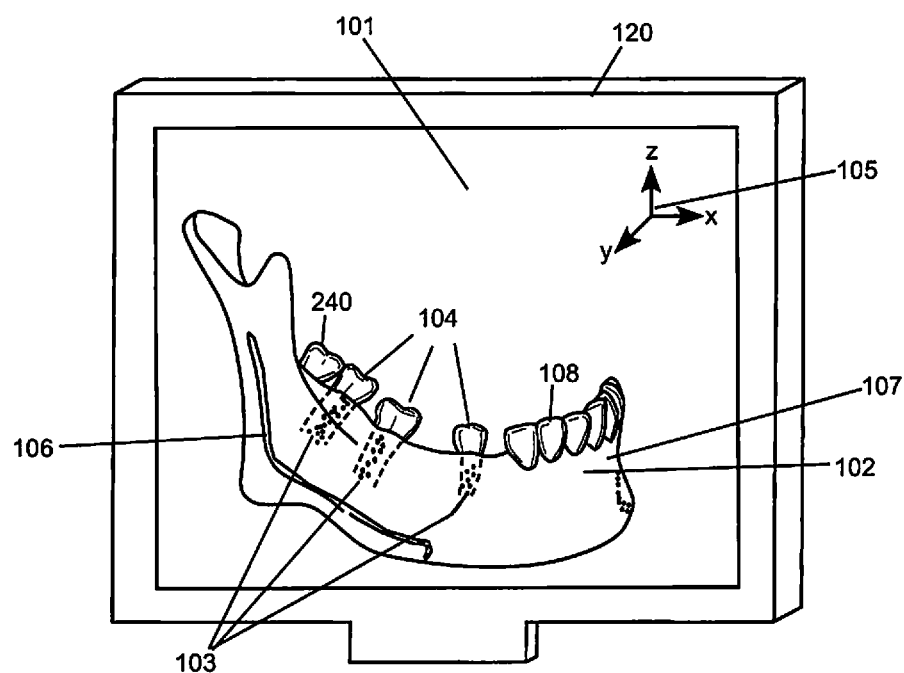
FIG. 1 depicts anatomical image of a patient's Computed Tomography (CT) scan rendered in planning software according to some embodiments presently disclosed.

FIG. 1 illustrates an exemplary anatomical image of a patient's CT scan rendered in planning software, according to some embodiments presently disclosed. According to some embodiments, a patient's anatomical image 102 such as CT scan image is rendered in three dimensions using a planning software 101 on a computer display 120 of a computer 215 (shown in FIG. 2b). The planning software 101 allows the doctor to visualize the patient's anatomy in a virtual space and create a virtual plan. In the virtual plan, the doctor is able to place one or more virtual implants 103 at exact desired locations within patient's anatomy. According to some embodiments, the planning software 101 also renders other objects 104 such as abutments and planned final restorations, together with the trajectory of the implants. According to some embodiments, the planning software 101 also renders vital structures such as a mandibular nerve 106 and provides/depicts spatial relationship between the mandibular nerve 106, virtually placed implants 103 and other objects 104 with the patient's anatomy. This establishes the three-dimensional final plan of the virtual implants 103 and objects 104. According to some embodiments, information such as trajectory, distances between objects, vital anatomical structures can be calculated and displayed to the doctor using, for example, the planning software 101.

According to some embodiments, an optical-based tracking system presently disclosed comprises an optical sensor coupled with a dental instrument, for example, a drill. In some embodiments, the optical sensor is configured to send data to a computer running algorithms that compare the exact location of teeth or markers in previously obtained dicom files from a CT scan to the surface anatomy of the patient's teeth or markers. In some embodiments, the navigation algorithm is configured to process the data from the optical sensor and calculate three-dimensional (3D) location of the dental instruments in patient's mouth. In some embodiments, the navigation algorithm is configured to show real-time positioning of the dental instrument with respect to the virtual plan. In some embodiments, the navigation algorithm tracks the position of the instrument in reference to the patient anatomy and sends visual feedback to doctor in real time.

Figures 2A, 2B:
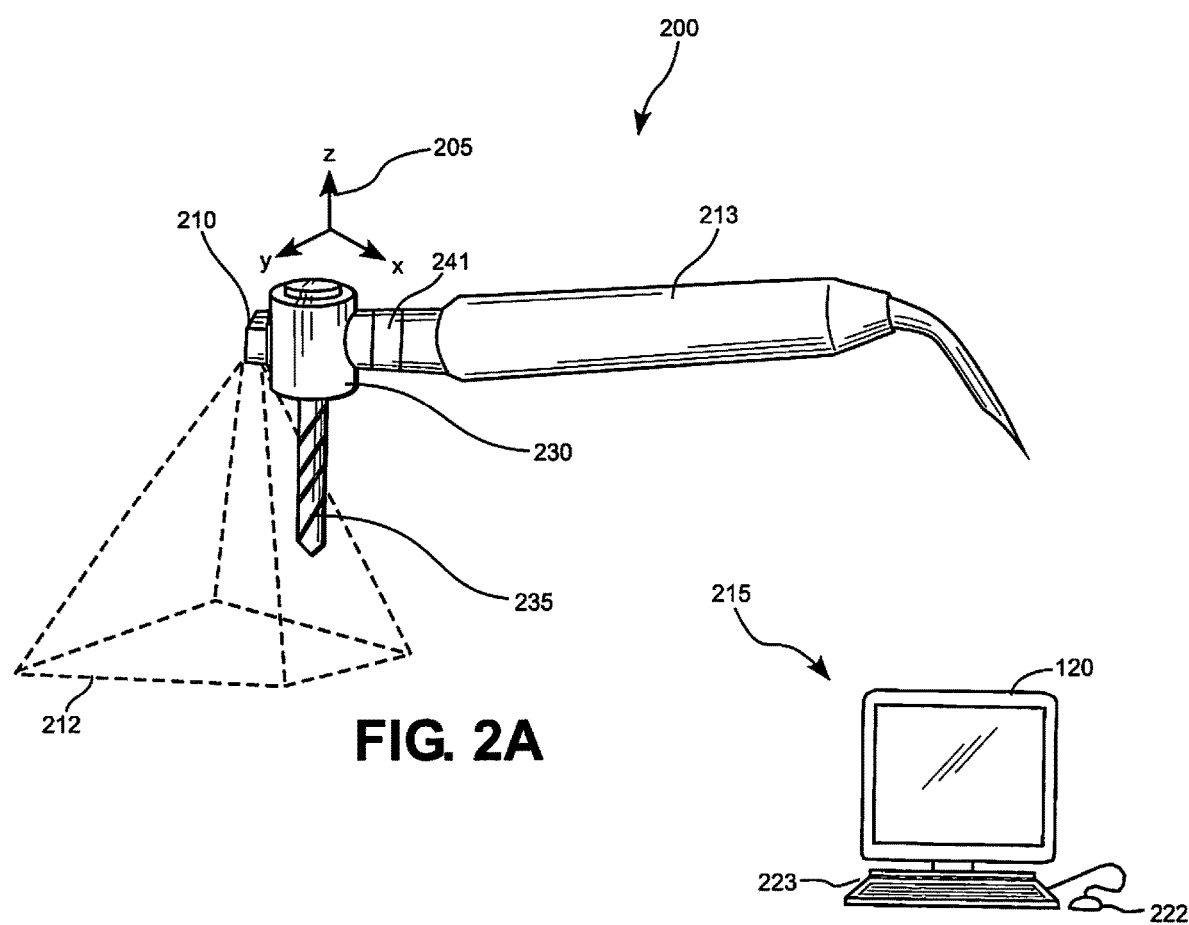
FIGS. 2a-b depict an embodiment according to the present disclosure.

According to some embodiments, an optical-based tracking system 200 presently disclosed is shown in FIG. 2a. According to some embodiments, the optical-based tracking system 200 comprises an optical sensor 210. According to some embodiments, the optical sensor 210 is coupled with dental instrument 213.

According to some embodiments, the dental instrument 213 is a drill. According to some embodiments, the drill 213 has a hand piece 230 couple with the optical sensor 210. According to some embodiments, the optical sensor 210 is coupled with the hand piece 230. According to some embodiments, the optical sensor 210 is part of the housing of the hand piece 230. According to some embodiments, the hand piece 230 accepts various burrs 235 of different diameters and lengths. According to some embodiments, the hand piece 230 accepts various burrs 235 of different diameters and lengths for preparing, for example, an osteotomy at a planned implant site of the patient. According to some embodiments, the various burrs 235 used during preparation of the site are automatically recognized and identified by the hand-piece 230 as such. According to some embodiments, the display 120 depicts the selected burr, with all its characteristics such as type, length and diameter.

According to some embodiments, the optical sensor 210 digitizes images of objects such as teeth or markers within an image plane 212, and transmits the images to the computer 215 (shown in FIG. 2b) running an algorithm to superimpose and merge the datasets obtained by the optical sensor 210 and the previously obtained data sets of the CT scan in dicom format. According to some embodiments, the computer 215 comprises a display 120 and one or more user input devices such as, for example, a mouse 222 or a keyboard 223.

Figure 3:
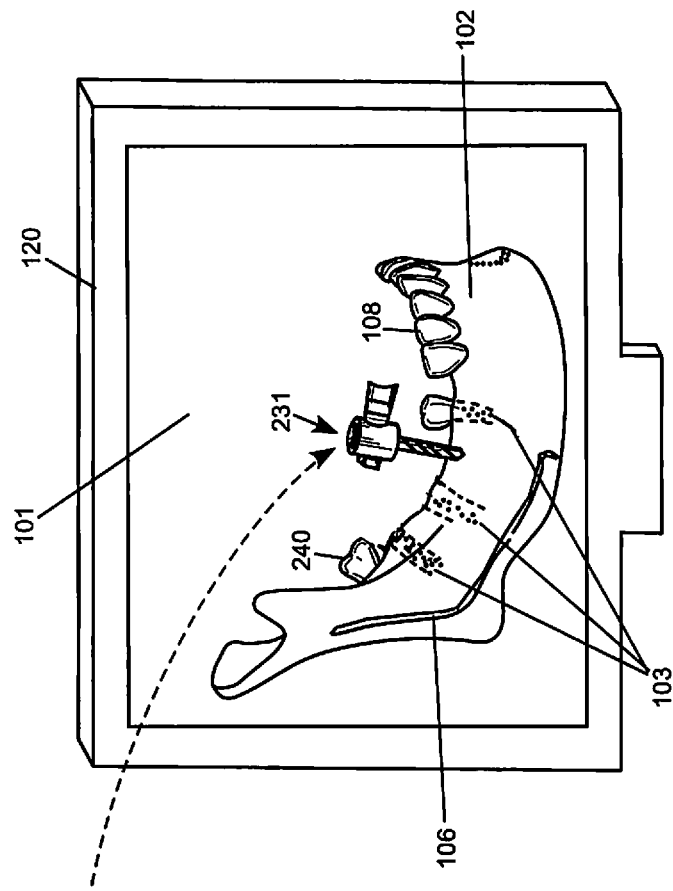
FIG. 3 depicts another embodiment according to the present disclosure.
Figure 3:
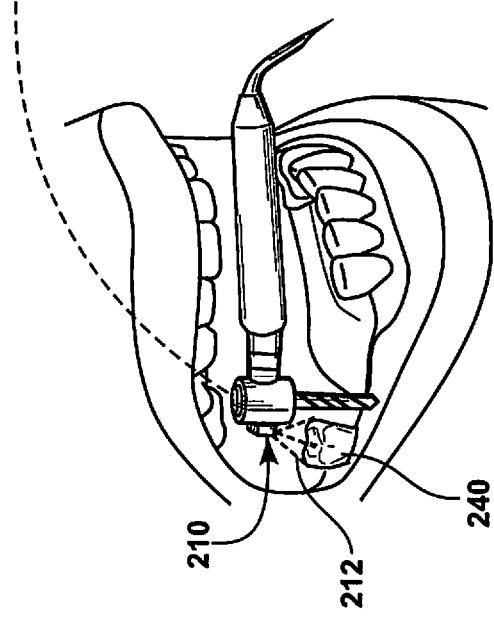

According to some embodiments, the optical sensor 210 is inserted into a mouth of a patient (as shown in FIG. 3) and the imaging plane 212 is passed over one or more intraoral structures 240 or markers (not shown) at a suitable distance to acquire surface scan/data from one or more teeth or other markers. According to some embodiments, the one or more intraoral structures 240 are one or more teeth, one or more crowns, and/or one or more implants in the patient's mouth. According to some embodiments, the markers (not shown) are one or more features placed by a doctor or another medical professional inside the patient's mouth to be used as a reference by the optical sensor 210. According to some embodiments, the markers (not shown) are one or more removable features placed by a doctor or another medical professional inside the patient's mouth to be used as a reference by the optical sensor 210.

According to some embodiments, the data set of the surface scan obtained in the oral cavity is merged with the previously obtained CT data set in real time. According to some embodiments, intra-oral structures 240 are superimposed using a surface algorithm onto the dicom data sets from the patient's CT scan, resulting in a merged real time picture. As the drill bits 235 are recognized to their specific shape, size and diameter via a detection mechanism 241 incorporated into the dental instrument 213, the exact outline relevant to length and diameter is projected over the anatomic picture 102 of the patient. If no virtual planning was done prior to treatment, virtual implants 103 will not be available. However, every one skilled in the art recognizes that although not planned previously, anatomic structures such as the mandibular nerve 106 or the cortical plates 107 and adjacent teeth 108 are readily visible and can be avoided. According to some embodiments, the virtual implants 103 have been planned in the planning software 101 and can be followed and superimposed with the real time image.

According to some embodiments, multiple different reformatted sections of the previously obtained dicom data sets are displayed on the computer 120 such as, but not limited to, coronal, saggital and panoramic sections. Thus the surgeon in real time can guide the location of the drill 235 to avoid adjacent anatomic structures such as nerves 106, adjacent teeth 108, cortical plates 107, and maxillary sinus amongst others. Alternatively, the surgeon can follow the previously planned virtual implant location 103 in length, angulation, trajectory and ultimately, final implant position.

According to some embodiments, communications between the computer 215 and the optical sensor 210 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, ultrasound or other wireless communication medium. In medical imaging or other sensitive applications, wireless image transmission from the optical sensor 210 to the computer 215 may be secured. The computer 215 may generate control signals to the optical sensor 210 which, in addition to image acquisition commands, may include conventional camera controls such as focus or zoom.

According to some embodiments, the optical sensor 210 may acquire two-dimensional image sets at a video rate while the optical sensor 210 is passed over a surface of the one or more intraoral structures 240 or markers (not shown). The two-dimensional image sets may be forwarded to the computer 215 for derivation of three-dimensional point clouds.

The three-dimensional data for each newly acquired two-dimensional image set may be derived and fitted or "stitched" to existing three-dimensional data using a number of different techniques. One useful example of such a technique is described in U.S. application Ser. No. 11/270,135, filed on Nov. 9, 2005, the entire contents of which is incorporated herein by reference. However, it will be appreciated that this example is not limiting, and that the principles described herein may be applied to a wide range of three-dimensional image capture systems. It will also be understood that terms such as "video" or "video rate" imply a wide range of possible frame rates associated with such video. While most modern video formats employ a frame rate of 25 to 30 frames per second, early video employed frame rates as low as 8 frames per second, and movies of the early 1900's varied from 12 to 18 frames per second. In addition, it is common for specialized imaging equipment to employ a rate adapted to the computational demands of particular imaging and rendering techniques, and some video systems operate with frame rates anywhere from 4 frames per second (for computationally extensive imaging systems) to 100 frames per second or higher (for high-speed video systems). As used herein, the terms video rate and frame rate should be interpreted broadly. Notwithstanding this broad meaning, it is noted that useful and visually pleasing three-dimensional imaging systems have been constructed according to the foregoing with frame rates of at least ten frames per second, frame rates of at least twenty frames per second, and frame rates between 25 and 30 frames per second.

It will be appreciated that the ability of certain systems, such as multi-aperture camera systems, to derive three-dimensional data from two-dimensional video image sets may depend in part on an ability to establish correspondence of surface points between image pairs (or triplets, and so on). The process of establishing point correspondences may be improved by identifying, within the processing system, unique features of the surface upon which correspondence may be based. In certain aspects, distinguishing features of teeth at varying levels of detail may be employed to enhance this process. However, this process depends on an ability to locate such distinguishable features. The process of establishing point correspondences may also, or instead, be enhanced by the addition of optically detectable features thereto, which may be as simple as artificial black dots distributed over a white or relatively light surface. In a dental context, this may be achieved with a spray, powder, mouth rinse, or the like that distributes optically detectable matter across the dentition or other dental object to be scanned. By randomly distributing such small, distinguishable dots across the surface, the likelihood of locating distinguishable features in a particular image set may be significantly improved, thus improving the speed and accuracy of the overall three-dimensional data acquisition process.

From time to time in continuous or incremental data acquisition systems, the fitting or stitch between two frames may fail. In such situations, a user may be notified through visual feedback that a recover mode has been entered. In the recover mode, the optical sensor 210 may seek to reacquire the previous scan by test fitting new scan data to previously acquired data, and providing visual feedback to a user to assist in navigating back to a scan location on the subject where the re-acquisition is being attempted. In a related landing mode, a user may attempt to initiate a new scan registered or connected to an existing three-dimensional model. Similar visual feedback tools may be provided to guide a user to an appropriate scan location, and notify a user when the scan has been reacquired. These techniques are described in greater detail in U.S. application Ser. No. 11/383,623, filed on May 16, 2006, incorporated herein by reference in its entirety. Other suitable techniques may be employed for navigation, controlling scan quality, analyzing scanned subject matter, and manipulating scanned models, various embodiments of which are described in greater detail below.

According to some embodiments, the display 120 may include any display suitable for video or other rate rendering at a level of detail corresponding to the acquired data or a rendered version of the acquired data. Suitable displays include cathode ray tube displays, liquid crystal displays, light emitting diode displays, plasma displays, and the like. In some embodiments, the display may include a touch screen interface using, for example capacitive, resistive, or surface acoustic wave (also referred to as dispersive signal) touch screen technologies, or any other suitable technology for sensing physical interaction with the display 120. In addition, where three-dimensional visualization is desired, the display 120 may include a three-dimensional display using a wide variety of techniques including stereo pair imaging, holographic imaging, and multiplanar or volumetric imaging, each with a number of rendering modalities that may be usefully employed with the systems described herein.

According to some embodiments, the optical sensor 210 may, through a continuous acquisition process, capture a point cloud of surface data having sufficient spatial resolution and accuracy to calculate three-dimensional (3D) surface points of the dental instrument 213 in patient's mouth based on the previously obtained and reconstructed CT scan. According to some embodiments, three-dimensional (3D) coordinates 205 may be obtained from data generated by the optical sensor 210. According to some embodiments, the coordinates 205 provide position and orientation represented in three-dimensional Cartesian coordinates (x, y, z) and orientation angles (azimuth, elevation, roll). According to some embodiments, the optical sensor 210 transmits data to the computer 215. According to some embodiments, the computer 215 is configured to generate three-dimensional (3D) coordinates 205 for the optical sensor 210 based on data from the optical sensor 210. According to some embodiments, the computer 215 is configured to generate three-dimensional (3D) coordinates 205 for the dental instrument 213 based on data from the optical sensor 210. According to some embodiments, three-dimensional (3D) coordinates for the dental instrument 213 correspond to the three-dimensional (3D) coordinates 205 associated with the optical sensor 210.

According to some embodiments, the computer 215 is configured to correlate the three-dimensional (3D) coordinates 205 with the patient CT coordinate system 105 and track position and orientation of the dental instrument 213 relative to the patient CT coordinate system 105.

According to some embodiments, the computer 215 is configured to transform the three-dimensional (3D) coordinates 205 to the patient CT scan coordinate system 105. According to some embodiments, the three-dimensional coordinate 205 of a point or an object in the patient's oral cavity can be represented in any coordinate system using, for example, a rigid body transformation matrix. For example, anatomical structure and other virtual objects such as implants in the patient's oral cavity can be transformed into the patient CT scan coordinate system 105, or vice versa.

According to some embodiments, the patient CT coordinate system 105 is used to track the dental instrument 213 during a surgery. In this case, any object represented in the coordinate system 205 is transformed into the patient CT coordinate system 105. According to some embodiments, any physical object in a real space registered with respect to any coordinate system can be represented by the three-dimensional coordinate as long as the relationship or the transformation matrix is known.

According to some embodiments, the coordinate system 205 may be defined by a distance between optical sensor 210 and one or more teeth, implants, static anatomical structure or artificial markers coupled to one or more teeth in the patient's oral cavity. The patient CT coordinate system 105 established in CT scan data is defined by the CT scan imaging software. According to some embodiments, the position and orientation of the dental instrument 213 is transformed into the patient CT coordinate system 105.

According to some embodiments, the optical sensor 210 comprises a camera suitable for capturing images from which a three-dimensional point cloud may be recovered. For example, the optical sensor 210 may employ a multi-aperture system as disclosed, for example, in U.S. Pat. Pub. No. 20040155975 to Hart et al., the entire contents of which is incorporated herein by reference. While Hart discloses one multi-aperture system, it will be appreciated that any multi-aperture system suitable for reconstructing a three-dimensional point cloud from a number of two-dimensional images may similarly be employed, including systems with moving apertures, fixed apertures, and/or electro-mechanically shuttered apertures. According to some embodiments, the optical sensor 210 comprises a plurality of apertures including a center aperture positioned along a center optical axis of a lens and any associated imaging hardware. According to some embodiments, the optical sensor 210 comprises a stereoscopic, triscopic or other multi-camera or other configuration in which a number of cameras or optical paths are maintained in fixed or moving relation to one another to obtain two-dimensional images of an object from a number of slightly different perspectives. According to some embodiments, the optical sensor 210 comprises suitable processing for deriving a three-dimensional point cloud from an image set or a number of image sets, or each two-dimensional image set may be transmitted to an external processor such as contained in the computer 215 described below. According to some embodiments, the optical sensor 210 comprises structured light, laser scanning, direct ranging (e.g., time of flight in a known direction), or any other technology suitable for acquiring three-dimensional data, or two-dimensional data that can be resolved into three-dimensional data.

FIG. 3 depicts an exemplary navigated surgical procedure, according to some embodiments presently disclosed. According to some embodiments, the computer 215 receives data from the optical sensor 210. The computer 215 matches the data sets from the CT scan and surface optical scan in real time and provides visualization on the display 120 showing planning software 101 for the doctor's visual feedback.

According to some embodiments, the system 200 is constantly updated on the display 120 showing planning software 101 to provide the doctor with a real time feedback of the instrument and drill position via drill detection mechanism 241 and orientation with respect to the patient's anatomy 102, implants 103, and/or any other reference point. This provides the doctor with a capability to visually track the position of the dental instrument 213 in the patient in real time. As the dental instrument 213 moves during a surgery, the position and orientation of the virtual instrument assembly 231 are updated in real time on the computer display showing planning software 101. During a surgery, if the accuracy of the instrument tracking is determined to be unreliable due to various factors, for example, the optical sensor 210 generates unreliable data, the planning software 101 displays a warning message to inform the doctor. In some embodiments, the planning software calculates and displays on the planning software 101 useful information for the doctor during the surgery such as the position and orientation offsets, an error to the intended drill trajectory while drilling, a distance to a vital structure in the patient's anatomy.

According to some embodiments, the dental instrument 213 has a feature that relays a feedback from the planning software, so the doctor does not have to look at the display showing planning software 101 and keeps his vision on the surgery. For example, the dental instrument 213 has a visual indicator, such as an LED light (not shown) or small LCD panel (not shown). The visual indicator provides the doctor with information such as drilling accuracy being within a tolerance or simply a warning if drill is too close to a vital anatomy of the patient. According to some embodiments, the dental instrument 213 has an audible feedback that provides an audible sound or haptic feedback that provides vibration or a tactile feedback to inform the doctor regarding the drilling accuracy or if drill is too close to vital anatomy of the patient.

Figure 5:
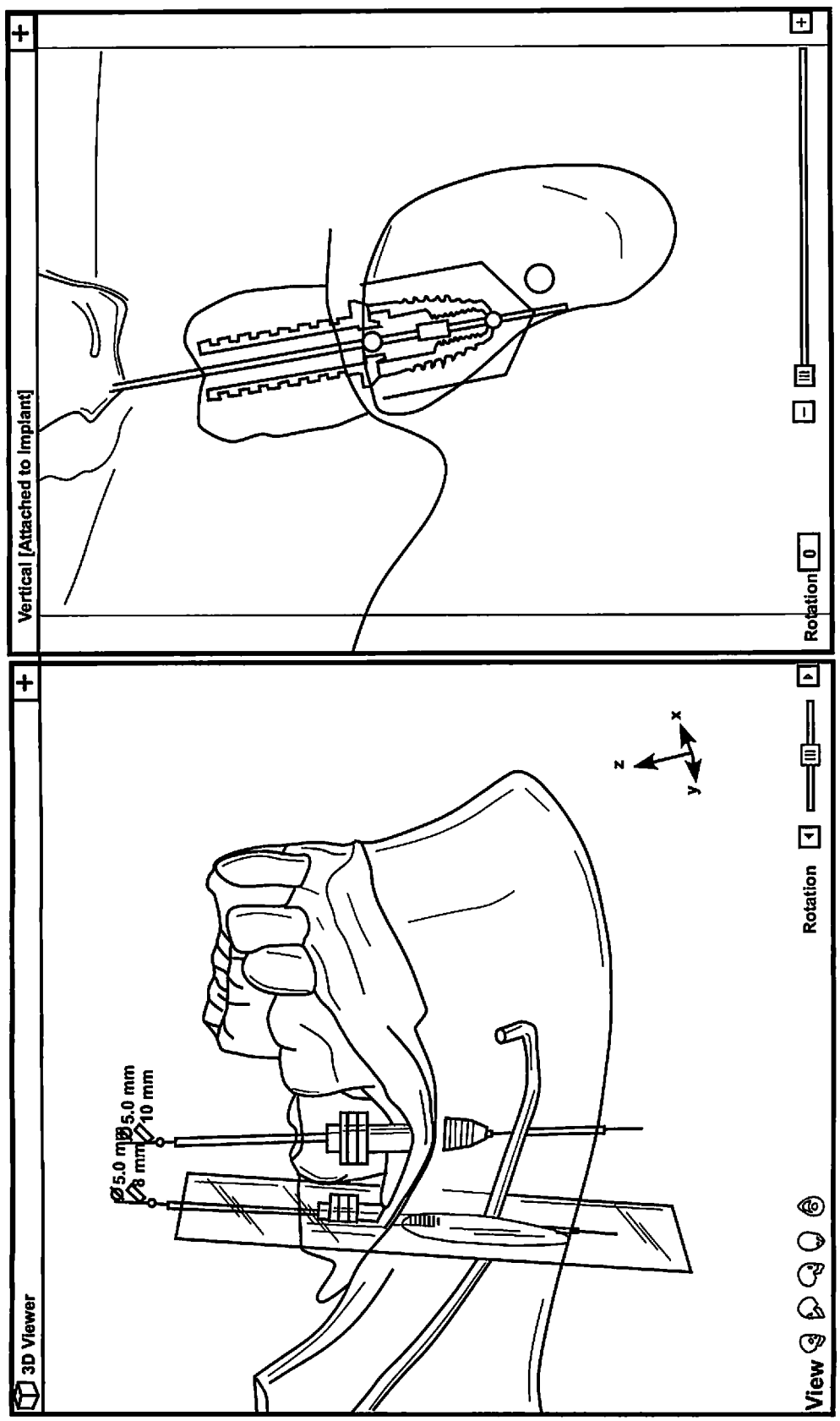
FIGS. 5-6 depict multiple views of the patient's anatomy for providing a doctor with a real time feedback of the instrument and drill position according to the present disclosure.
Figure 6:
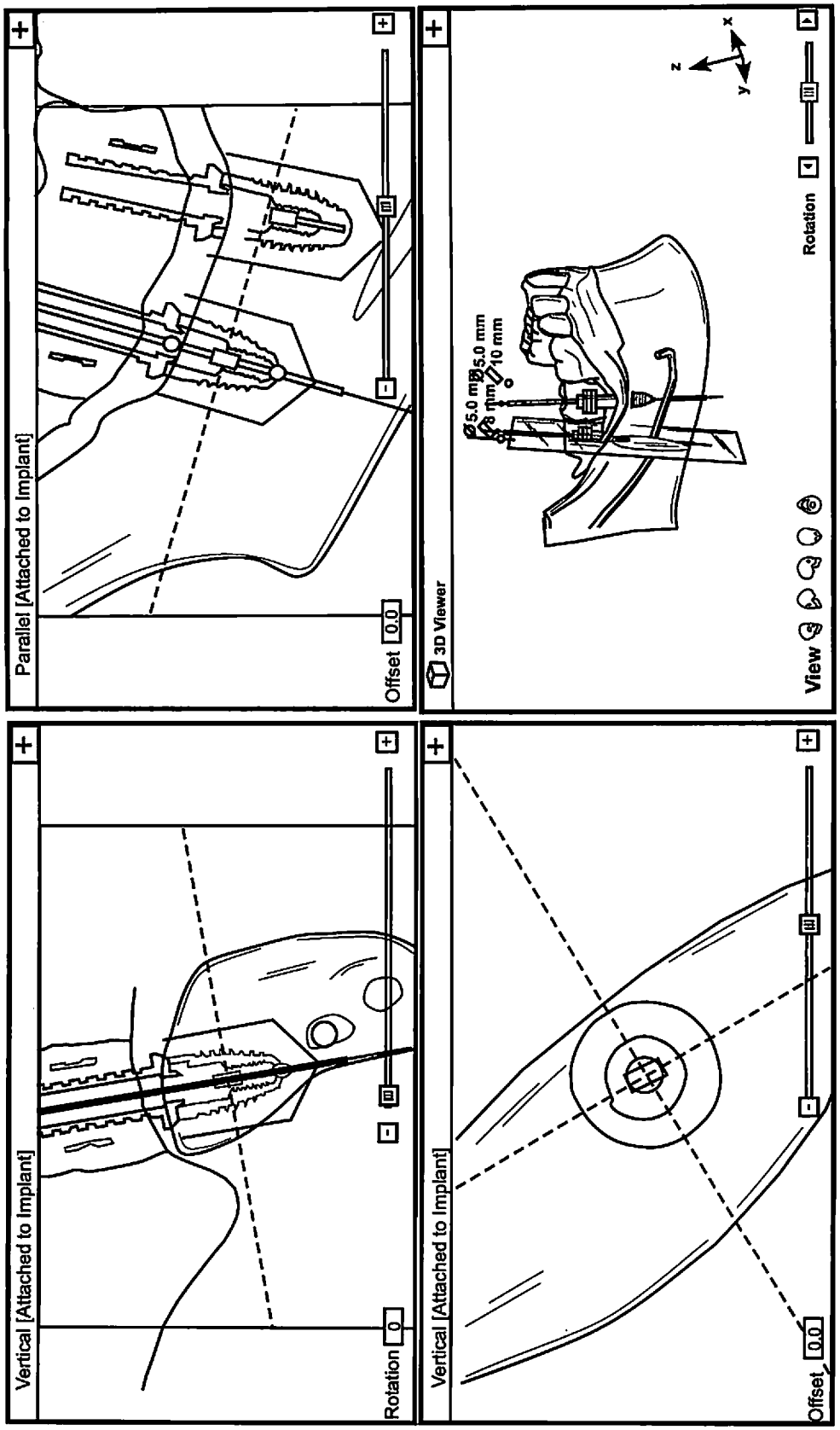

According to some embodiments, the display 120 depicts multiple views of the patient's anatomy 102 to provide the doctor with a real time feedback of the instrument and drill position as shown in FIGS. 5-6.

Figure 4A:
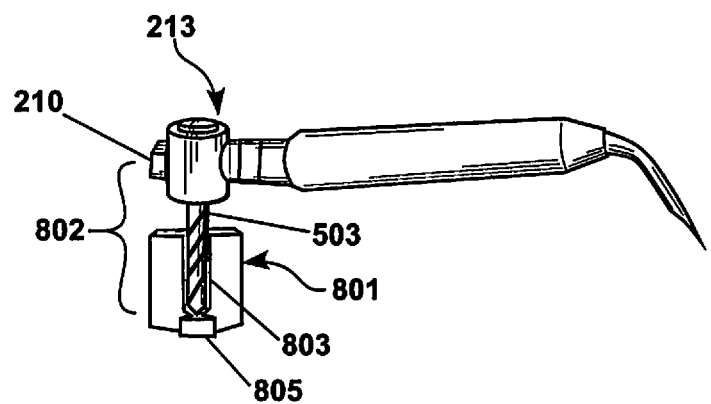
FIGS. 4a-b depict another embodiment according to the present disclosure.
Figure 4B:
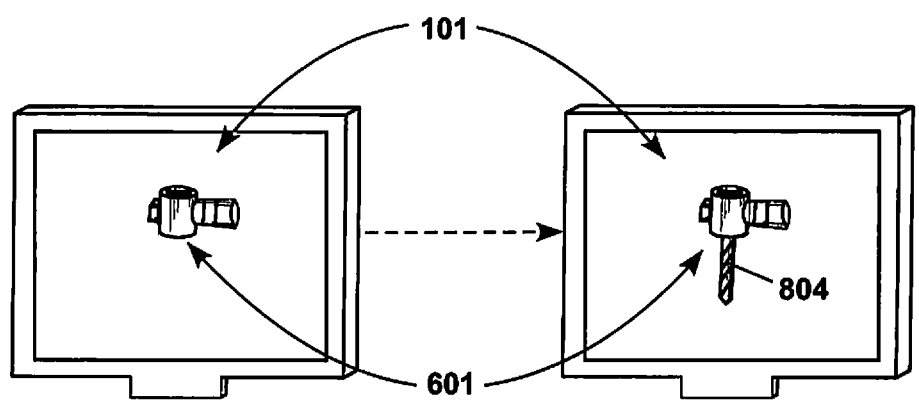

FIGS. 4a-b depict an exemplary procedure for registering dimensions of the dental instrument 213 according to some embodiments presently disclosed. For the dental instrument 213, a drill offset 802 from the optical sensor 210 to the tip of an attached drill bit 503 must be determined to register the drill position and orientation within the patient's oral cavity. According to some embodiments, a registration apparatus 801 of known dimensions may be used to register the drill offset 802. A drill bit 503 of the dental instrument 213 is inserted into the socket 803 of the registration apparatus 801. Another sensor 805 is attached to the registration apparatus 801 with a known position offset. The socket 803 has a physical stop that makes contact with the drill bit 503 when it is fully inserted. In this static position, the drill 503's critical features (e.g., tip length, position and orientation) are determined from the position and orientation data from the optical sensor 210 and geometric calculation. During a surgery, the drill bit 503 may be changed several times, and each drill bit may have a different length and size. According to some embodiments, the planning software 101 supports this drill registration to determine the drill shape whenever a new drill bit is used. This allows the virtual instrument assembly 601 to be accurately updated and the drill bit information is updated on the planning software 101 accordingly.

Figure 4C:
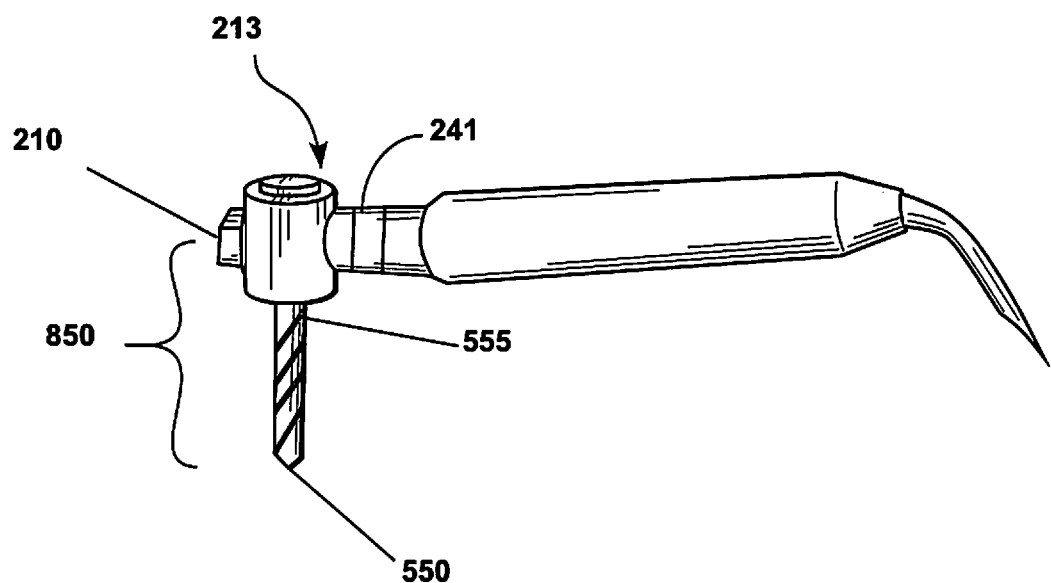

FIG. 4c depict another exemplary procedure for registering dimensions of the dental instrument 213 according to some embodiments presently disclosed. For the dental instrument 213, a drill offset 850 from the optical sensor 210 to the tip of an attached drill bit 550 must be determined to register the drill position and orientation within the patient's oral cavity. According to some embodiments, the drill bit 550 comprises one or more markings 555 to identify the length, diameter, and/or type of drill bit inserted into the instrument 213. According to some embodiments, the one or more markings 555 is a bars code. According to some embodiments, the optical sensor 210 is configured to identify the one or more markings 555 and identify the length, diameter, and/or type of drill bit 550 inserted into the instrument 213. According to some embodiments, the detection mechanism 241 is configured to identify the one or more markings 555 and identify the length, diameter, and/or type of drill bit 550 inserted into the instrument 213. According to some embodiments, the detection mechanism 241 is an optical sensor configured to monitor the drill bit 550.

According to some embodiments, the drill bits have different shaft configurations that allow the presently described system to identify the length, diameter and type of burr inserted into the instrument 213. FIGS. 4*d-f* depict top view of drill bits 560, 565 and 570. According to some embodiments, the drill bits 560, 565 and 570 comprise one or more markings 575. According to some embodiments, the one or more markings 575 are notches in the drill bits 560, 565 and 570. According to some embodiments, the one or more markings 575 are protrusions in the drill bits 560, 565 and 570. According to some embodiments, the presently described system is configured to identify the length, diameter and type of the drill bits 560, 565 and 570 based on the dimensions, number of and/or location of the one or more markings 575.

Referring to FIGS. 2*a-b*, according to some embodiments, the dental instrument 213 is a hand piece configured to accommodate various burrs 235. According to some embodiments, the hand piece 230 accepts various bits 235 of different diameters and lengths. According to some embodiments, the hand piece 230 accepts various bits 235 of different diameters and lengths for reducing volume of a tooth structure. According to some embodiments, the hand piece 230 accepts various bits 235 of different diameters and lengths for reducing volume of a bone. According to some embodiments, the various burrs 235 used during a procedure are automatically recognized and identified by the handpiece 230 as such (as described above). According to some embodiments, the display 120 depicts the selected burr, with all its characteristics such as type, length and diameter.

Figure 7:
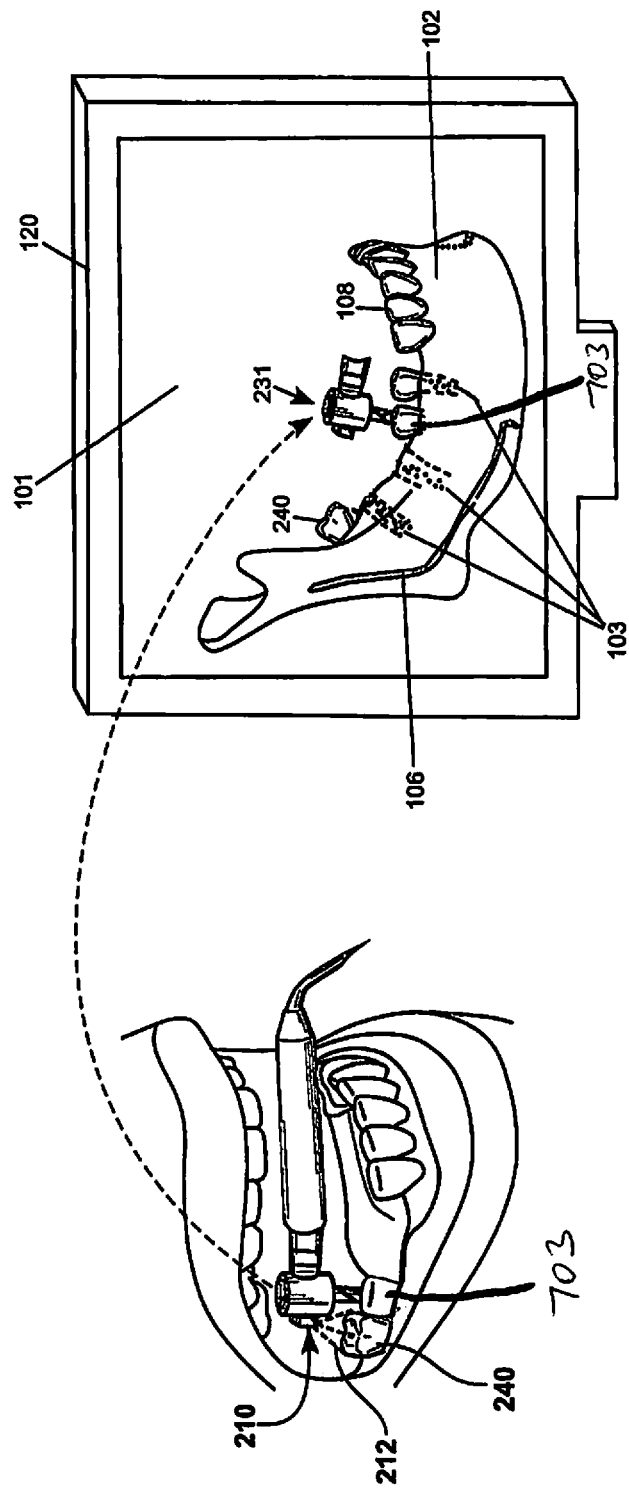
FIG. 7 depicts another embodiment according to the present disclosure.

According to some embodiments, the optical sensor 210 is inserted into a mouth of a patient (as shown in FIG. 7) and the imaging plane 212 is passed over one or more intraoral structures 240 or markers (not shown) at a suitable distance to acquire surface scan/data from one or more teeth or other markers. According to some embodiments, the one or more intraoral structures 240 are one or more teeth, one or more crowns, and/or one or more implants in the patient's mouth. According to some embodiments, the markers (not shown) are one or more features placed by a doctor or another medical professional inside the patient's mouth to be used as a reference by the optical sensor 210. According to some embodiments, the markers (not shown) are one or more removable features placed by a doctor or another medical professional inside the patient's mouth to be used as a reference by the optical sensor 210.

According to some embodiments, the data set of the surface scan obtained in the oral cavity is merged with the previously obtained CT data set in real time. According to some embodiments, intra-oral structures 240 are superimposed using a surface algorithm onto the dicom data sets from the patient's CT scan, resulting in a merged real time picture. As the bit 235 is recognized to its specific shape, size and diameter via a detection mechanism as described above, the exact outline relevant to length and diameter is projected over the anatomic picture 102 of the patient. According to some embodiments, reduction of volume of the tooth structure 703 has been planned in the planning software 101 and can be followed and superimposed with the real time image. According to some embodiments, the surgeon in real time can reduce the volume of the tooth structure 703 to match the planned structure represented in the planning software 101.

FIG. 7 depicts an exemplary navigated surgical procedure, according to some embodiments presently disclosed.

According to some embodiments, the computer 215 receives data from the optical sensor 210. The computer 215 matches the data sets from the CT scan and surface optical scan in real time and provides visualization on the display 120 showing planning software 101 for the doctor's visual feedback.

According to some embodiments, the system 200 is constantly updated on the display 120 showing planning software 101 to provide the doctor with a real time feedback of the instrument and burr position via drill detection mechanism 241 and orientation with respect to the patient's anatomy 102, implants 103, and/or any other reference point. This provides the doctor with a capability to visually track the position of the dental instrument 213 in the patient in real time. As the dental instrument 213 moves during a surgery, the position and orientation of the virtual instrument assembly 231 are updated in real time on the computer display showing planning software 101. During a surgery, if the accuracy of the instrument tracking is determined to be unreliable due to various factors, for example, the optical sensor 210 generates unreliable data, the planning software 101 displays a warning message to inform the doctor. In some embodiments, the planning software calculates and displays on the planning software 101 useful information for the doctor during the surgery such as the position and orientation offsets, an error to the intended drill trajectory while drilling, a distance to a vital structure in the patient's anatomy.

According to some embodiments, the dental instrument 213 has a feature that relays a feedback from the planning software, so the doctor does not have to look at the display showing planning software 101 and keeps his vision on the surgery. For example, the dental instrument 213 has a visual indicator, such as an LED light (not shown) or small LCD panel (not shown). The visual indicator provides the doctor with information such as tooth structure volume removal accuracy being within a tolerance or simply a warning if the doctor is about to remove unnecessary part of the tooth structure. According to some embodiments, the dental instrument 213 has an audible feedback that provides an audible sound or haptic feedback that provides vibration or a tactile feedback to inform the doctor regarding the tooth structure volume removal accuracy.

According to some embodiments, the optical-based tracking system 200 further comprises an optical sensor-cleaning member (not shown). According to some embodiments, the optical sensor-cleaning member (not shown) is coupled with dental instrument 213. According to some embodiments, the optical sensor-cleaning member (not shown) is configured to spray gas to remove any debris that may be at least partially covering/blocking the optical sensor 210. According to some embodiments, the optical sensor-cleaning member (not shown) is configured to spray liquid to remove any debris that may be at least partially covering/blocking the optical sensor 210. According to some embodiments, the optical sensor-cleaning member (not shown) is configured to spray gas and/or liquid to remove any debris that may be at least partially covering/blocking the optical sensor 210. According to some embodiments, the gas is air or compressed air. According to some embodiments, the liquid is water. According to some embodiments, the debris is blood, bone, and/or any other matter present in the patients mouth during procedure.

It is also understood that the registration of an instrument assembly can be performed in a variety of ways using a sensor, a transmitter, and/or a combination of a sensor and a transmitter in a similar way as described above without deviating the scope of the present subject matter.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ."

What is claimed is:

1. A dental drill comprising:
   a drill bit comprising one or more markings, wherein the drill bit is removably coupled with the dental drill;
   a detection mechanism coupled with the dental drill; wherein the detection mechanism is configured to determine information about the drill bit based on the one or more markings;
   an optical sensor configured to acquire a surface data from one or more intraoral structures;
   a processing unit configured to merge the optical sensor data with a Computed Tomography (CT) data set from a CT scan of the one or more intraoral structures; and
   a display displaying the one or more intraoral structures superimposed onto the CT scan based on the merging of the optical sensor data with a Computed Tomography (CT) data set and displaying position of the drill bit based on the merging of the optical sensor data with a Computed Tomography (CT) data set.

2. The dental drill of claim 1, wherein the detection mechanism is another optical sensor.

3. The dental drill of claim 1, wherein the one or more markings is a bar code.

4. The dental drill of claim 1, wherein the one or more markings is a notch.

5. The dental drill of claim 1 wherein the one or more markings is a protrusion.

6. The dental drill of claim 1, wherein the detection mechanism is configured to determine a length of the drill bit, a diameter of the drill bit, or a type of drill bit based on the dimensions, number of or location of the one or more markings.

7. The dental drill of claim 1, wherein the detection mechanism is configured to determine a length of the drill bit, a diameter of the drill bit, and a type of drill bit inserted into the dental drill.

* * * * *